United States Patent
Hartwich et al.

(10) Patent No.: US 10,660,843 B2
(45) Date of Patent: May 26, 2020

(54) INTENSIVE HAIR CONDITIONER WITH POSITIVE EFFECT ON CURL DEFINITION

(71) Applicant: Henkel AG & Co. KGaA, Duesseldorf (DE)

(72) Inventors: Christa Hartwich, Elmshorn (DE); Christin von Borstel, Drochtersen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/201,731

(22) Filed: Nov. 27, 2018

(65) Prior Publication Data
US 2019/0159998 A1 May 30, 2019

(30) Foreign Application Priority Data
Nov. 29, 2017 (DE) .......................... 10 2017 221 361

(51) Int. Cl.
| | | |
|---|---|---|
| *A61K 8/88* | (2006.01) | |
| *A61K 8/81* | (2006.01) | |
| *A61Q 5/06* | (2006.01) | |
| *A61Q 5/12* | (2006.01) | |
| *A61K 8/41* | (2006.01) | |
| *A61K 8/891* | (2006.01) | |

(52) U.S. Cl.
CPC ................ *A61K 8/88* (2013.01); *A61K 8/416* (2013.01); *A61K 8/8152* (2013.01); *A61K 8/8158* (2013.01); *A61K 8/8176* (2013.01); *A61K 8/8182* (2013.01); *A61K 8/891* (2013.01); *A61Q 5/06* (2013.01); *A61Q 5/12* (2013.01); *A61K 2800/594* (2013.01)

(58) Field of Classification Search
CPC ........................................................ A61K 8/88
See application file for complete search history.

(56) References Cited

U.S. PATENT DOCUMENTS

| | | | | |
|---|---|---|---|---|
| 4,859,456 A | * | 8/1989 | Marschner | ............. A61K 8/416 424/47 |
| 8,597,623 B2 | * | 12/2013 | Hoffmann | ............. A61K 8/416 424/401 |
| 2013/0309190 A1 | * | 11/2013 | Dimotakis | ............... A61Q 5/06 424/70.17 |

FOREIGN PATENT DOCUMENTS

| | | |
|---|---|---|
| GB | 2559222 A | 8/2018 |
| WO | 2005020942 A2 | 3/2005 |

* cited by examiner

*Primary Examiner* — Kyle A Purdy
(74) *Attorney, Agent, or Firm* — Lorenz & Kopf, LLP

(57) ABSTRACT

The present disclosure relates to a cosmetic agent for treating keratin fibres, in particular human hair, wherein the cosmetic agent in a cosmetic carrier comprises a first polymer, which is a polyimide, and a second polymer, which is a film former, wherein the pH value of the cosmetic agent lies between about 2 and about 5 and the viscosity lies between about 8000 and about 25000 mPa s.

18 Claims, No Drawings

INTENSIVE HAIR CONDITIONER WITH POSITIVE EFFECT ON CURL DEFINITION

CROSS-REFERENCE TO RELATED APPLICATION

This application claims priority to German Patent Application No. 10 2017 221 361.2, filed Nov. 29, 2017, which is incorporated herein by reference in its entirety.

TECHNICAL FIELD

The present disclosure relates to cosmetic agents for the treatment of keratin fibres, in particular human hair, wherein the cosmetic agent in a cosmetic carrier contains a polyimide and a film former. The present disclosure also relates to a method for nourishing and shaping keratin fibres, in particular human hair, comprising applying the cosmetic agent. The present disclosure additionally relates to the use of the cosmetic agent for nourishing and shaping or for nourishing and firming keratin fibres.

BACKGROUND

The stress on hair is increasing constantly. The reasons for this are many. On the one hand, fashion trends are short-lived and require constant hairstyle changes, and on the other hand a repeated dyeing or a repeated use of permanent waving are a strain on hair. Not least, environmental burdens generally signify a stress for hair. These stresses lead to a need for care products that regenerate hair or in which the hair also merely appears to be nourished or feels nourished. The latter increases the sense of wellbeing of the user.

High requirements are placed on the known active substances or active substance combinations. A continuously increasing requirement profile is created since not only are requirements in respect of the nourishment of the hair to be satisfied, but the satisfaction of further requirements is also expected.

User expectation is focused on hairstyle hold for example. Here, all of the hair should remain in an advantageous form. If the keratin fibres are human hair, reference is also made to a strong hairstyle hold or a high degree of hold of the cosmetic agent. Cosmetic compositions that comprise polymers are often used for a strong hairstyle hold and are adsorbed onto the hair and give it a hold of this kind. When a strong hairstyle hold is required, such cosmetic compositions are used by being applied to the hair for temporary re-shaping and left there. Reference is therefore also made to what are known as "leave-in" treatments or compositions.

There is also a need, however for cosmetic agents that merely simplify the styling, that is to say a desired shaping. With use of such agents, substances from the cosmetic agents remain on the surface of the hair once the hair has been rinsed and facilitate the shaping, but in this case for example during hair drying, which is performed subsequently to the hair treatment with the cosmetic agent. In the case of cosmetic agents with which a treatment is performed which is followed subsequently by a rinsing out with water, reference is also made to "rinse off" compositions.

The choice of active substance combinations and compositions in cosmetic agents is also dependent on the hair type, i.e. on whether the user has fine, dry or stressed hair. The development of active substance combinations and compositions is also dependent on whether they are intended for use on curly or smooth hair. Particularly in the case of curly hair, there is a need for improvements in respect of nourishment and hold.

The problem forming the basis of the present disclosure lies in providing a cosmetic agent having a nourishing and at the same time holding effect. In particular, the hairstyle hold in the case of curly hair is to be improved.

BRIEF SUMMARY

Cosmetic agents for treating keratin fibres and methods for nourishing and shaping keratin fibres are provided herein. In an embodiment, a cosmetic agent for treating keratin fibres includes, in a cosmetic carrier, (a) at least one first polymer comprising the structural units of formulas M1, M2 and M3

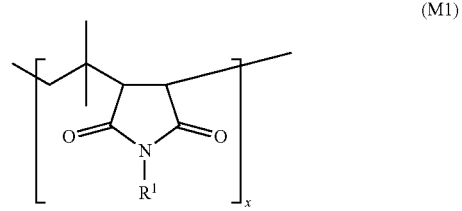

(M1)

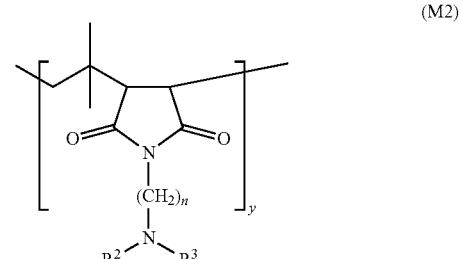

(M2)

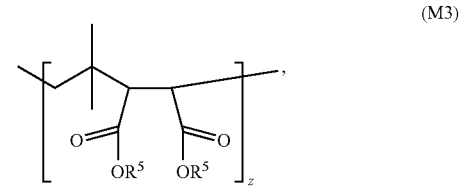

(M3)

wherein $R^1$ is a group comprising oxyalkylene groups, $R^2$ and $R^3$ independently of one another are an alkyl group comprising from about 1 to about 3 C atoms, n is a number between from about 1 and about 5, and $R^4$ and $R^5$ independently of one another are hydrogen or an alkyl group comprising from about 1 to about 3 C atoms, with the proviso that either $R^4$ and $R^5$ are hydrogen or one of $R^4$ and $R^5$ is hydrogen, wherein x, y and z each lie between about 0.05 and about 0.95 parts wherein the sum of x, y and z is equal to about 1, and (b) at least one second polymer, which is a film former, wherein the pH value of the cosmetic agent is between about 2 and about 5, and the viscosity is between about 8000 and about 25000 mPa s, measured at 20° C. with a Brookfield viscometer DV-II, spindle 6 at 20 rpm.

In another embodiment, a cosmetic agent for treating keratin fibres includes, in a cosmetic carrier, (a) at least one first polymer comprising the structural units of formulas M1, M2 and M3

(M1)

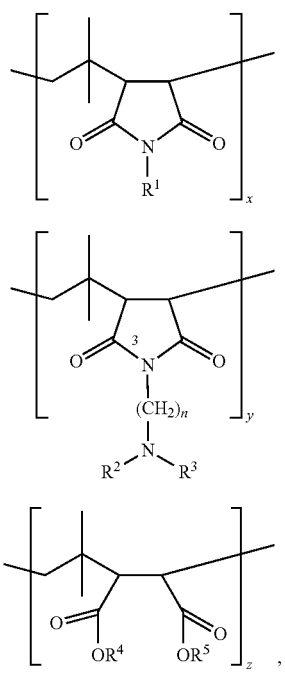

(M2)

(M3)

wherein
R¹ is chosen from a group of general formula M4

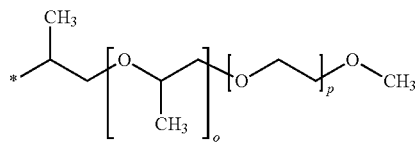

(M4)

in which o and p are each a number between about 1 and about 50,

R² and R³ independently of one another are an alkyl group comprising from about 1 to about 3 C atoms, n is a number between from about 1 and about 5, and R⁴ and R⁵ independently of one another are hydrogen or an alkyl group comprising from about 1 to about 3 C atoms, with the proviso that either R⁴ and R⁵ are hydrogen or one of R⁴ and R⁵ is hydrogen, wherein x, y and z each lie between about 0.05 and about 0.95 parts wherein the sum of x, y and z is equal to about 1, wherein the first polymer is included in the cosmetic agent in an amount of from about 0.01 to about 2 wt. %, and (b) at least one second polymer, which is a film former, wherein the second polymer representing the film former is derived from the monomer units 1-vinyl-2-pyrrolidone and vinyl acetate, wherein the second polymer representing the film former is included in the cosmetic agent in an amount of from about 1 to about 9 wt. % in relation to the total weight of the cosmetic agent, wherein the pH value of the cosmetic agent is between from about 3 and about 4 and the viscosity is between 12000 and 16000, measured at 20° C. with a Brookfield viscometer DV-II, spindle 6 at 20 rpm.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The problem forming the basis of the present disclosure is solved by the subject matter of claim 1. A first subject of the present disclosure is therefore a cosmetic agent for the treatment of keratin fibres, in particular human hair, wherein the cosmetic agent in a cosmetic carrier comprises (a) at least one first polymer containing the structural units of formulas M1, M2 and M3

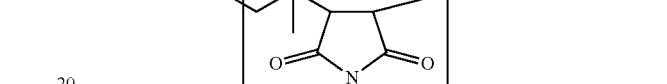
(M1)

(M2)

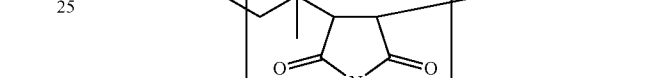
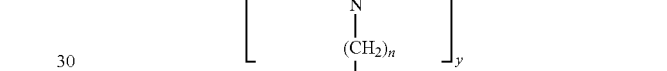
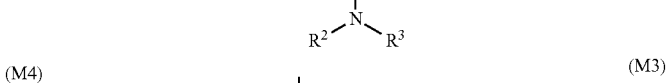
(M3)

wherein
R¹ is a group containing oxyalkylene groups,

R² and R³ independently of one another are an alkyl group comprising from about 1 to about 3 C atoms and n is a number between about 1 and about 5, and R⁴ and R⁵ independently of one another are hydrogen or an alkyl group comprising from about 1 to about 3 C atoms, with the proviso that either R⁴ and R⁵ are hydrogen or one of R⁴ and R⁵ is hydrogen, wherein x, y and z each lie between about 0.05 and about 0.95 parts when the sum of x, y and z is equal to about 1, and (b) at least one second polymer, which is a film former, wherein the pH value of the cosmetic agent is from about 2 to about 5, preferably from about 3 to about 4, and the viscosity is from about 8000 to about 25000 mPa s, preferably from about 10000 to about 20000, more preferably from about 12000 to about 16000 (measured at 20° C. with a Brookfield viscometer DV-II, spindle 6 at 20 rpm).

It has surprisingly been found that the first polymer, which is a terpolymer, or optionally a polymer comprising more than three monomer units, gives the hair, together with a film former, nourishing properties and at the same time holding properties. In particular, an emphasis is placed on a lasting natural look of curls and a nourishing effect thereon. These properties can be attributed, inter alia, to an improved distribution of the nourishing constituents on the hair.

Polymers that fall under the definition of the first polymer are known and can fall under the INCI name "Isobutylene/dimethylaminopropyl maleimide/ethoxylate d maleimide/maleic acid copolymer". In the first polymer the three monomer units M1, M2 and M3 are distributed along the polymer backbone. The monomer units each contribute by four carbon atoms to the structure of the polymer backbone. The variables x, y and z reflect the proportions of the respective monomer units. A person skilled in the art will of course understand the proportions to be substance amount fractions. If, for example, x is equal to about 0.1, about 10% of all monomer units in the first polymer thus constitute the monomer unit M1.

In accordance with the present disclosure the cosmetic agent comprises a film former. Film formers are understood to mean those polymers which, as they dry, leave behind a continuous film on the skin, the hair, or the nails. Film formers of this type can be used in the widest range of different cosmetic products, such as face masks, make-up, hair setting agents, hairsprays, hair gels, hair waxes, intensive hair conditioners, shampoos, or nail varnishes. Polymers which have a sufficient solubility in water, alcohol or water/alcohol mixtures are preferred. Corresponding solutions which can be used or further processed in a simple way can thus be produced.

Within the scope of the present disclosure a film former is understood to mean in particular those polymers which, when used in from about 0.05 to about 20 wt. % (in relation to the total weight of the cosmetic agent) aqueous, alcoholic or aqueous-alcoholic solution, are capable of being deposited on the hair in a transparent polymer film.

The cosmetic agent is exemplified by a pH value of from about 2 to about 5, preferably from about 3 to about 4. The cosmetic agent is thus suitable for use as a rinse. The combination of the polyimide as first polymer and the film former as second polymer is selected such that, even at the set pH values, a stable composition that can be easily produced and easily handled is provided.

The cosmetic agent is exemplified by a viscosity of from about 8000 to about 25000 mPa s, preferably from about 10000 to about 20000 mPa s, more preferably from about 12000 to about 16000 mPa s. The viscosities of the cosmetic agents are measured in accordance with the Brookfield method, measured in each case at 20° C. with a Brookfield viscometer spindle 6 at 20 rpm).

The viscosities of the cosmetic agent tend to lie above the usual values for conventional hair rinse products. This is intended to increase customer acceptance of use of the cosmetic agent as a "leave-in" treatment. Users prefer to apply compositions of higher viscosity, since they associate a better efficacy therewith. The viscosity values also make it easier to distribute the cosmetic agent in the head hair. Whereas the pH value of the cosmetic agent set as contemplated herein constitutes the feature that the cosmetic agent can be suitable for use as a hair rinse, i.e. as a "rinse-off" treatment, the cosmetic agent is additionally well suited for a "leave-in" treatment on account of the set viscosity. The user can thus choose between these uses.

Within the scope of the present disclosure, keratin fibres are understood to mean fur, wool, feathers and in particular human hair.

In cosmetic agents a polyimide that is preferably used as first polymer is one in which the structural units M1, M2 or M3 are selected from those in which the group $R^1$ containing oxyalkylene groups is a group containing one or more oxyethylene groups and a group comprising one or more oxypropylene groups, more preferably a group of general formula M4

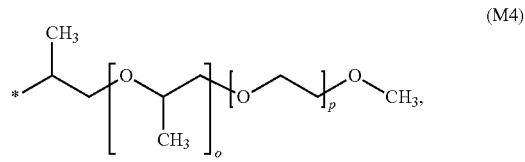

in which o and p are each a number between about 1 and about 50, even more preferably a number between about 1 and about 20, most preferably a number between about 1 and about 8, or in which the groups $R^2$ and $R^3$ are each a methyl group and/or n is equal to about 3, or in which the groups $R^4$ and $R^5$ are either hydrogen or one of $R^4$ and $R^5$ is an ethyl group. In other words, the groups $R^4$ and $R^5$—are either both hydrogen or one of the groups is hydrogen and the other is an ethyl group. The polyimide therefore contains, in one or more side chains, ethylene oxide and propylene oxide groups, which are distributed randomly along the side chain. The polyimides of this preferred embodiment are particularly readily available. The most preferred polyimides may fall under the INCI name "Isobutylene/dimethyl aminopropyl maleimide/ethoxylated maleimide/maleic acid copolymer".

In a preferred embodiment the first polymer is contained in the cosmetic agent in an amount of from about 0.01 to about 2 wt. %, preferably in an amount of from about 0.05 to about 1 wt. %, more preferably in an amount of from about 0.1 to about 0.8 wt. %, most preferably in an amount of from about 0.2 to about 0.5 wt. %, in each case in relation to the total weight of the cosmetic agent.

As described above, the combination of the polyimide as first polymer and the film former as second polymer is selected such that a stable composition that can be easily produced and easily handled is provided also at the set pH values. This is also true for the viscosities, i.e. the first polymer and the second polymer are selected such that stable compositions that can be easily produced are provided also at the set viscosities. At the pH values and the viscosities, the first and second polymer should emphasise the advantageous effects associated with the polymers.

In accordance with a preferred embodiment of the present disclosure the film former, i.e. the second polymer, is derived from one or more monomer units comprising 1-vinyl-2-pyrrolidone, preferably is derived from the monomer units 1-vinyl-2-pyrrolidone and vinyl acetate, more preferably is derived from the monomer units 1-vinyl-2-pyrrolidone and vinyl acetate in a ratio of 1-vinyl-2-pyrrolidone to vinyl acetate of greater than 1. In particular, polymers or copolymers comprising polyvinylpyrrolidone or polyvinylpyrrolidone/polyvinyl acetate demonstrate advantageous properties in combination with the above polyimide. The feature in accordance with which the ratio of 1-vinyl-2-pyrrolidone to vinyl acetate is greater than 1 shall be understood by a person skilled in the art to mean that the copolymer formed of the monomers 1-vinyl-2-pyrrolidone and vinyl acetate includes a higher molar proportion of the monomer unit 1-vinyl-2-pyrrolidone. In particular, the non-ionogenic nature of this film former could be conducive to solving the problem forming the basis of the present disclosure together with the first polymer.

Within the scope of the present disclosure, the expression in accordance with which polymers are derived from monomers shall always be understood to mean that the monomers or monomer units build the polymer, i.e. the polymer is produced by an arbitrary polymerisation of the corresponding monomers.

In a preferred embodiment the second polymer constituting the film former is contained in the cosmetic agent in an amount of from about 1 to about 9 wt. %, preferably in an amount of from about 2 to about 8 wt. %, more preferably in an amount of from about 4 to about 6 wt. %, in each case in relation to the total weight of the cosmetic agent.

It is particularly preferred that the ratio of the amount of first polymer to the amount of second polymer is less than about 1. In other words, particularly preferably more film former is used as polyimide. In yet a further preferred embodiment of the present disclosure, the ratio of the amount of first polymer to the amount of second polymer is less than from about 1 to about 2, most preferably less than from about 1 to about 10. The combination of polyimide with the preferred film formers has proven to be particularly advantageous for solving the problem forming the basis of the present disclosure. The ratio of the amounts of first polymer to second polymer shall be a ratio by weight within the scope of the present disclosure. Both the preferred amounts of first and second polymer and also the proportion of first polymer to second polymer contribute to solving the problems forming the basis of the present disclosure.

In a further embodiment the cosmetic agent contains a third polymer which is different from the first and second polymer. The cosmetic agent preferably contains a third polymer, which is a homopolymer comprising a poly(meth)acrylate with a quaternary ammonium alkylene group as ester side chain and a cosmetically acceptable counter ion, in particular a halide as counter ion. Homopolymers of this kind have proven to be particularly suitable thickeners which are particularly well compatible with the selected first and second polymers. The third polymer is particularly preferably a homopolymer derived from the monomer N, N, N-trimethyl-2-((2-methyl-1-oxo-2-propenyl)oxy)chloride.

In accordance with a preferred embodiment the third polymer is contained in the cosmetic agent in an amount of from about 0.1 to about 5 wt. %, preferably in an amount of from about 0.5 to about 2.5 wt. %, and more preferably in an amount of from about 1 to about 2 wt. %, in each case in relation to the total weight of the cosmetic agent. In particular in the case of the used first and second polymers, the use of the referred third polymer in the preferred amounts is particularly well suited for providing the cosmetic agent in the desired viscosity.

The nourishing effect of the compositions as contemplated herein can be intensified or modified by the incorporation of further nourishing active substances. Silicone compounds, i.e. polyorganosiloxanes, are preferably contained as further nourishing substances in the cosmetic agent. In a preferred embodiment the cosmetic agent contains at least one first and one second siloxane, in each case comprising the structural units M5,

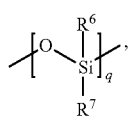

(M5)

wherein the first siloxane is preferably a low-molecular siloxane with q equal to from about 4 to about 12, more preferably from about 6 to about 10, in which $R^6$ and $R^7$ are selected identically or differently from one another from H or an alkyl group comprising from about 1 to about 4 C atoms, more preferably in which $R^6$ and $R^7$ are the same and are a methyl group, and/or wherein the second siloxane is preferably a branched or unbranched polysiloxane with q greater than or equal to about 20, in which $R^6$ and $R^7$ are selected identically or differently from one another from H or an alkyl group comprising from about 1 to about 4 C atoms, more preferably in which $R^6$ and $R^7$ are the same and are a methyl group, and/or wherein the second siloxane is preferably a polysiloxane with a viscosity of from about 15 to about 200 cSt, more preferably from about 20 to about 100 cSt, in particular of approximately 50 cSt.

The first siloxane is intended to improve the compatibility of the second siloxane with the cosmetic carrier. Many polyorganosiloxanes of higher molecular weight are insoluble in water, but have a positive nourishing effect on the hair. The compatibility of the polyorganosiloxanes with a higher molecular weight, i.e. of the second siloxane, with an aqueous carrier can be improved with the low-molecule siloxanes, i.e. first siloxanes, which tend to be better soluble in water.

In accordance with this preferred embodiment the first siloxane and the second siloxane shall contain the monomer unit M5, wherein other monomer units can also be provided in the first siloxane or second siloxane. The siloxanes can thus be branched, i.e. the siloxanes can comprise a monomer unit in which a silicon atom carries just one organic group R and carries a further silicon atom, instead of the second organic group, which further silicon atom is part of a polyorganosiloxane group. The improved properties of the cosmetic agent of this preferred embodiment are also demonstrated when combing and untangling wet hair.

The first siloxane is more preferably a dimethicone, in particular a cyclic dimethicone.

In order to determine the viscosity of the second siloxane, a ball drop viscometer is used. With the aid of this apparatus, the viscosity of the second siloxane can be determined with use of DIN 53015. To facilitate the determination of which polysiloxanes can be used as second siloxanes in the cosmetic agent as contemplated herein, the manufacturer's instructions in respect of viscosity of the polysiloxanes were used. The used polysiloxanes are all commercially obtainable and are classified as conventional in respect of their viscosities, measures in Stokes.

In accordance with a preferred embodiment of the cosmetic agent the first siloxane is contained in the cosmetic agent in an amount of from about 0.5 to about 8 wt. %, preferably from about 1 to about 5 wt. %, more preferably from about 2 to about 3 wt. %, in relation to the total weight of the cosmetic agent, and/or the second siloxane is contained in the cosmetic agent in an amount of from about 1 to about 10 wt. %, preferably from about 2 to about 8 wt. %, more preferably from about 4 to about 6 wt. %, in relation to the total weight of the cosmetic agent. If the cosmetic agent contains the first and second siloxane in the above preferred amounts, a cosmetic agent results into which on the one hand the siloxanes can be mixed in a stable manner, and on the other hand an advantageous nourishing effect can be attained. The latter is manifested, inter alia, in an improved combability of the hair following use of the cosmetic agent.

In order to intensify the effects as contemplated herein, the cosmetic agents preferably additionally contain at least one surfactant. Non-ionic, anionic, cationic, and/or ampholytic surfactants can generally be contained. The group of ampholytic or amphoteric surfactants comprises zwitterionic surfactants and ampholytes. It has proven to be particularly advantageous if the cosmetic agents additionally contain at least one cationic surfactant in order to increase the hair-nourishing properties. In accordance with a preferred embodiment the cosmetic agent contains one or more quaternary ammonium compounds. These are the cationic surfactants. The cosmetic agent particularly preferably contains a cationic surfactant, wherein the cationic surfactant is preferably constituted by one or more quaternary ammonium compounds which have two or more fatty acid ester groups, in each case with an acyl group comprising from about 12 to about 20 C atoms, and/or which have a molecular weight of about 750 g/mol or more. The molecular weight is a valid summary measure for the number and length of the fatty acid ester groups of the quaternary ammonium compound. Quaternary ammonium compounds having at least this molecular weight are used advantageously in the cosmetic agent. Such cationic surfactants are obtainable for example under the name Dehyquart® F-75 T.

Cationic surfactants of the type constituted by the ester-quats, the imidazolines, and the amidoamines can be used with preference. Preferred quaternary ammonium compounds are ammonium halides, in particular chlorides and bromides, such as alkyl trimethyl ammonium chlorides, dialkyl dimethyl ammonium chlorides, and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride, and the imidazolium compounds known under the INCI names Quaternium-27 and Quaternium-83. The long alkyl chains of the above-mentioned surfactants preferably have from about 12 to about 20 carbon atoms.

Esterquats are known substances that contain both at least one ester function and at least one quaternary ammonium group as structural element. Preferred esterquats are quaternised ester salts of fatty acids with triethanolamine, quaternised ester salts of fatty acids with diethanolalkylamines, and quaternised ester salts of fatty acids with 1,2-dihydroxy-propyldialkylamines. Such products are sold for example under the trademarks Stepantex®, Dehyquart® and Armocare®. The products Armocare® VGH-70, an N,N-bis(2-palmitoyloxyethyl)dimethylammonium chloride, and Dehyquart® F-75, Dehyquart® C-4046, Dehyquart® L80 and Dehyquart® AU-35 are examples of such esterquats. The cosmetic agent particularly preferably contains an ammonium compound known under the (INCI) name Distearoylethyl Hydroxyethylmonium Methosulfate.

As further cationic surfactants, the agents as contemplated herein can contain at least one quaternary imidazoline compound, i.e. a compound that has a positively charged imidazoline ring. The formula (F1) presented below shows the structure of these compounds.

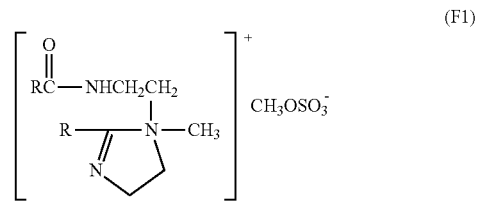
(F1)

The groups R stand, independently of one another, for a saturated or unsaturated, linear or branched hydrocarbon group with a chain length of from about 10 to about 30 carbon atoms. The preferred compounds of formula 1 contain the same hydrocarbon group for R in each case. The chain length of the groups R is preferably about 12 carbon atoms. Compounds with a chain length of at least about 16 carbon atoms and very particularly preferably with at least about 20 carbon atoms are particularly preferred. In the formula (F1) methosulfate is presented as counter ion. In accordance with the present disclosure, however, the halides such as chloride, fluoride, bromide, or also phosphates are also included as counter ions.

The cationic surfactants are contained in the cosmetic agent preferably in amounts of from about 0.05 to about 10 wt. %, more preferably in amounts of from about 0.5 to about 5 wt. %, most preferably in amounts of from about 1 to about 3 wt. %, in each case in relation to the total weight of the cosmetic agent.

In a further preferred embodiment of the present disclosure the cosmetic agent contains at least one nourishing oil. Oils as nourishing substances are advantageous, since they give the hair a silky sheen and make the hair more resistant by smoothing the surface of the hair. Nourishing oils, however, place greater requirements on the product formulation since they have to be incorporated in a stable manner with no sign of a disadvantageous settling or creaming during longer storage periods of product containers.

In accordance with a preferred embodiment of the present disclosure the cosmetic agent comprises at least one nourishing oil and/or at least one nourishing constituent, more preferably at least one natural nourishing oil, i.e. a substance comprising a triglyceride of natural origin, wherein plant-based nourishing oil(s)/nourishing constituent(s) is/are particularly preferred. Nourishing constituents should be of the non-polymeric kind.

Plant-based nourishing oils from the group of amaranth seed oil, argan oil, rice germ oil, baobab oil, Manketti oil, manila seed oil, yangu seed oil, rambutan oil, buckthorn oil, monoi oil, tigernut oil, inca inchi oil, avocado oil, cottonseed oil, cupuacu butter, cashew oil, safflower oil, peanut oil, jojoba oil, chamomile oil, coconut oil, pumpkin seed oil, linseed oil, macadamia oil, corn oil, almond oil, apricot kernel oil, poppy seed oil, evening primrose oil, olive oil, rapeseed oil, soybean oil, sunflower oil, and wheat germ oil, in particular (---)-α-bisabolol, hydrogenated jojoba oil and/or coconut oil are particularly preferred. The cosmetic agent comprises D-panthenol as a particularly preferred nourishing constituent. The advantage of these nourishing oils or nourishing constituents lies in the fact that they originate to the greatest possible extent from natural sources and are thus energy- and resource-preserving raw materials. In accordance with the preferred embodiment the cosmetic agent can contain, in relation to the total weight, from about 0.0005 to about 3 wt. %, preferably from about 0.001 to about 2 wt. %, and particularly preferably from about 0.05 to about 1 wt. % of the sum of nourishing oils and nourishing constituent.

In further preferred embodiments of the present disclosure the cosmetic agent also contains preservatives, fragrance and optionally further auxiliaries.

The cosmetic agent contains the above-described ingredients in a cosmetic carrier that is water-based. This is understood within the scope of the present disclosure to mean preferably an aqueous or aqueous-alcoholic carrier. The cosmetic agent preferably contains at least about 50 wt. %, more preferably at least about 65 wt. %, particularly preferably at least about 70 wt. %, and particularly preferably at least about 75 wt. % water.

The problem forming the basis of the present disclosure is solved by a second subject of the present disclosure, which is therefore a method for nourishing and shaping keratin fibres, in particular human hair, comprising the following steps:

applying a cosmetic agent as contemplated herein to the keratin fibres, in particular hair, in a first step, and leaving the cosmetic agent on the keratin fibres, in particular human hair, or rinsing the keratin fibres, in particular human hair, with water in a second step.

In the method as contemplated herein, the cosmetic agent as contemplated herein is applied to the keratin fibres, in particular to the human hair, in a first step. In particular, the agent as contemplated herein can be applied to the previously wetted hair. The step of the application can be improved by applying the agent uniformly.

In the second step either the cosmetic agent is left on the keratin fibres, in particular on human hair, and then the method would correspond to a "leave-in" treatment, or in the second step the keratin fibres, in particular human hair, are rinsed with water, and then the method would correspond to a "rinse off" treatment. It is one of the advantageous effects that the cosmetic agent can be used both in a "eave-in" and in a "rinse-off" treatment and attains a visible effect.

If, in the second step, the keratin fibres, in particular human hair, are rinsed, the applied cosmetic agent can be left on the keratin fibres, in particular human hair, for a period of time of from about 5 second to about 30 minutes, more preferably from about 30 seconds to about 10 minutes, even more preferably from about 1 minute to about 5 minutes on the keratin fibres, in particular human hair, in a preferred embodiment of the present disclosure. In this preferred embodiment of the present disclosure the cosmetic agent in a second step is left on the keratin fibres, in particular human hair, and is rinsed with water. This represents a special form of a "rinse-off" treatment.

The problem forming the basis of the present disclosure is solved by a third subject of the present disclosure, which is therefore the use of the cosmetic agent as contemplated herein for nourishing and shaping or for nourishing and holding keratin fibres, in particular human hair.

In a preferred embodiment of the present disclosure the cosmetic agent as contemplated herein is used to nourish and shape curly human hair. The cosmetic agent demonstrates the advantageous effects best in the case of curly and/or wavy hair.

In accordance with the present disclosure, very particularly preferred cosmetic agents comprise at least one of the following embodiments A) to G):

A)
A cosmetic agent for treating keratin fibres, in particular human hair, wherein the cosmetic agent in a cosmetic carrier comprises (a) at least one first polymer containing the above-presented structural units of formulas M1, M2 and M3, wherein R1 is a group of the general, above-described formula M4 containing oxyalkylene groups, in which o and p are each a number between about 1 and about 50, more preferably a number between about 1 and about 20, even more preferably a number between about 1 and about 8; R2 and R3 are a methyl group and n is equal to about 3; and R4 and R5-independently of one another are hydrogen or an ethyl group, or one of R4 and R5 is hydrogen and the other is an ethyl group, wherein x, y and z each lie between about 0.05 and about 0.95 parts when the sum of x, y and z is equal to about 1, and (b) at least one second polymer, which is a film former, wherein the pH value of the cosmetic agent is between about 2 and about 5, preferably between about 3 and about 4, and the viscosity is between about 8000 and about 25000 mPa s, preferably between about 10000 and about 20000, more preferably between about 12000 and about 16000 (measured at 20° C. with a Brookfield viscometer DV-II, spindle 6 at 20 rpm).

B)
A cosmetic agent for treating keratin fibres, in particular human hair, wherein the cosmetic agent in a cosmetic carrier comprises (a) at least one first polymer containing the above-presented structural units of formulas M1, M2 and M3, wherein R1 is a group of the general, above-described formula M4 containing oxyalkylene groups, in which o and p are each a number between about 1 and about 50, more preferably a number between about 1 and about 20, even more preferably a number between about 1 and about 8; R2 and R3 are a methyl group and n is equal to about 3; R4 and R5 independently of one another are hydrogen or an ethyl group, or one of R4 and R5 is hydrogen and the other is an ethyl group, wherein x, y and z each lie between about 0.05 and about 0.95 parts when the sum of x, y and z is equal to about 1, and (b) at least one second polymer, which is a film former, wherein the second polymer representing the film former is derived from one or more monomer units comprising 1-vinyl-2-pyrrolidone, or is derived from the monomer units 1-vinyl-2-pyrrolidone and vinyl acetate, wherein the pH value of the cosmetic agent is between about 2 and about 5, preferably between about 3 and about 4, and the viscosity is between about 8000 and about 25000 mPa s, preferably between about 10000 and about 20000, more preferably between about 12000 and about 16000 (measured at 20° C. with a Brookfield viscometer DV-II, spindle 6 at 20 rpm).

C)
A cosmetic agent for treating keratin fibres, in particular human hair, wherein the cosmetic agent in a cosmetic carrier comprises (a) at least one first polymer containing the above-presented structural units of formulas M1, M2 and M3, wherein R1 is a group of the general, above-described formula M4 containing oxyalkylene groups, in which o and p are each a number between about 1 and about 50, more preferably a number between about 1 and about 20, even more preferably a number between about 1 and about 8; R2 and R3 are a methyl group and n is equal to about 3; R4 and R5 independently of one another are hydrogen or an ethyl group, or one of R4 and R5 is hydrogen and the other is an ethyl group, wherein x, y and z each lie between about 0.05 and about 0.95 parts when the sum of x, y and z is equal to about 1, and (b) at least one second polymer, which is a film former, wherein the second polymer representing the film former is derived from one or more monomer units comprising 1-vinyl-2-pyrrolidone, or is derived from the monomer units 1-vinyl-2-pyrrolidone and vinyl acetate, wherein the ratio of the amount of first polymer to the amount of second polymer is less than about 1, preferably less than from about 1 to about 2, most preferably less than from about 1 to about 10, and wherein the pH value of the cosmetic agent is between about 2 and about 5, preferably between about 3 and about 4, and the viscosity is between about 8000 and about 25000 mPa s, preferably between about 10000 and about 20000, more preferably between about 12000 and about 16000 (measured at 20° C. with a Brookfield viscometer DV-II, spindle 6 at 20 rpm).

D)
A cosmetic agent for treating keratin fibres, in particular human hair, wherein the cosmetic agent in a cosmetic carrier comprises (a) at least one first polymer containing the above-presented structural units of formulas M1, M2 and M3, wherein R1 is a group of the general, above-described formula M4 containing oxyalkylene groups, in which o and p are each a number between about 1 and about 50, more preferably a number between about 1 and about 20, even more preferably a number between about 1 and about 8; R2 and R3 are a methyl group and n is equal to about 3; R4 and R5 independently of one another are hydrogen or an ethyl group, or one of R4 and R5 is hydrogen and the other is an ethyl group, wherein x, y and z each lie between about 0.05 and about 0.95 parts when the sum of x, y and z is equal to about 1, (b) at least one second polymer, which is a film former, wherein the second polymer representing the film former is derived from one or more monomer units comprising 1-vinyl-2-pyrrolidone, or is derived from the monomer units 1-vinyl-2-pyrrolidone and vinyl acetate, wherein the ratio of the amount of first polymer to the amount of second polymer is less than about 1, preferably less than from about 1 to about 2, most preferably less than from about 1 to about 10, and (c) a third polymer, which is a homopolymer comprising a poly(meth)acrylate with a quaternary ammonium alkylene group as ester side chain and a cosmetically acceptable counter ion, in particular a halide as counter ion, wherein the pH value of the cosmetic agent is between about 2 and about 5, preferably between about 3 and about 4, and the viscosity is between about 8000 and about 25000 mPa s, preferably between about 10000 and about 20000, more preferably between about 12000 and about 16000 (measured at 20° C. with a Brookfield viscometer spindle 6 at 20 rpm).

E)
A cosmetic agent for treating keratin fibres, in particular human hair, wherein the cosmetic agent in a cosmetic carrier comprises (a) at least one first polymer containing the above-presented structural units of formulas M1, M2 and M3, wherein R1 is a group of the general, above-described formula M4 containing oxyalkylene groups, in which o and p are each a number between about 1 and about 50, more preferably a number between about 1 and about 20, even more preferably a number between about 1 and about 8; R2 and R3 are a methyl group and n is equal to about 3; R4 and R5 independently of one another are hydrogen or an ethyl group, or one of R4 and R5 is hydrogen and the other is an ethyl group, wherein x, y and z each lie between about 0.05 and about 0.95 parts when the sum of x, y and z is equal to 1, (b) at least one second polymer, which is a film former, wherein the second polymer representing the film former is derived from one or more monomer units comprising 1-vinyl-2-pyrrolidone, or is derived from the monomer units 1-vinyl-2-pyrrolidone and vinyl acetate, wherein the ratio of the amount of first polymer to the amount of second polymer is less than about 1, preferably less than from about 1 to about 2, most preferably less than from about 1 to about 10, and (c) a cationic surfactant, and wherein the pH value of the cosmetic agent is between about 2 and about 5, preferably between about 3 and about 4, and the viscosity is between about 8000 and about 25000 mPa s, preferably between about 10000 and about 20000, more preferably between about 12000 and about 16000 (measured at 20° C. with a Brookfield viscometer spindle 6 at 20 rpm).

F)
A cosmetic agent for treating keratin fibres, in particular human hair, wherein the cosmetic agent in a cosmetic carrier comprises (a) at least one first polymer containing the above-presented structural units of formulas M1, M2 and M3, wherein R1 is a group of the general, above-described formula M4 containing oxyalkylene groups, in which o and p are each a number between about 1 and about 50, more preferably a number between about 1 and about 20, even more preferably a number between about 1 and about 8; R2 and R3 are a methyl group and n is equal to about 3; R4 and R5 independently of one another are hydrogen or an ethyl group, or one of R4 and R5 is hydrogen and the other is an ethyl group, wherein x, y and z each lie between about 0.05 and about 0.95 parts when the sum of x, y and z is equal to about 1, (b) at least one second polymer, which is a film former, wherein the second polymer representing the film former is derived from one or more monomer units comprising 1-vinyl-2-pyrrolidone, or is derived from the monomer units 1-vinyl-2-pyrrolidone and vinyl acetate, wherein the ratio of the amount of first polymer to the amount of second polymer is less than about 1, preferably less than from about 1 to about 2, most preferably less than from about 1 to about 10, and (c) a cationic surfactant, wherein the cationic surfactant is preferably a quaternary ammonium compound having two fatty acid ester groups in each case with an acyl group comprising from about 12 to about 20 C atoms, and wherein the pH value of the cosmetic agent is between about 2 and about 5, preferably between about 3 and about 4, and the viscosity is between about 8000 and about 25000 mPa s, preferably between about 10000 and about 20000, more preferably between about 12000 and about 16000 (measured at 20° C. with a Brookfield viscometer DV-II, spindle 6 at 20 rpm).

G)
A cosmetic agent for treating keratin fibres, in particular human hair, wherein the cosmetic agent in a cosmetic carrier comprises (a) at least one first polymer containing the above-presented structural units of formulas M1, M2 and M3, wherein R1 is a group of the general, above-described formula M4 containing oxyalkylene groups, in which o and p are each a number between about 1 and about 50, more preferably a number between about 1 and about 20, even more preferably a number between about 1 and about 8; R2 and R3 are a methyl group and n is equal to about 3; R4 and R5 independently of one another are hydrogen or an ethyl group, or one of R4 and R5 is hydrogen and the other is an ethyl group, wherein x, y and z each lie between about 0.05 and about 0.95 parts when the sum of x, y and z is equal to about 1, (b) at least one second polymer, which is a film former, wherein the second polymer representing the film former is derived from one or more monomer units comprising 1-vinyl-2-pyrrolidone, or is derived from the monomer units 1-vinyl-2-pyrrolidone and vinyl acetate, wherein the ratio of the amount of first polymer to the amount of second polymer is less than about 1, preferably less than from about 1 to about 2, most preferably less than from about 1 to about 10, and (c) at least one first and one second siloxane, in each case comprising the structural units

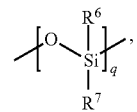

(M5)

wherein the first siloxane is a low-molecular siloxane with q equal to from about 4 to about 12, more preferably from about 6 to about 10, in which $R^6$ and $R^7$ are a methyl group, and wherein the second siloxane is preferably a branched or unbranched polysiloxane with q greater than or equal to about 20, in which $R^6$ and $R^7$ are a methyl group, and/or wherein the second siloxane is preferably a polysiloxane with a viscosity of from about 15 to about 200 cSt, more preferably from about 20 to about 100 cSt, in particular of approximately 50 cSt, and wherein the pH value of the cosmetic agent is between about 2 and about 5, preferably between about 3 and about 4, and the viscosity is between about 8000 and about 25000 mPa s, preferably between about 10000 and about 20000, more preferably between about 12000 and about 16000 (measured at 20° C. with a Brookfield viscometer DV-II, spindle 6 at 20 rpm).

Features relating to preferred embodiments of the first subject matter of the present disclosure which are described above only in this regard of course also apply accordingly as features of preferred embodiments for the second and third subject matter.

The following examples are intended to explain the subject matter of the present disclosure without limiting it in any way.

Examples

The following composition was produced in accordance with a formulation as contemplated herein:

| Raw material | E1* |
| --- | --- |
| Aquaflex ® XL-30[1] | 0.7 |
| PVP/VA copolymer 60/40 W[2] | 4.3 |
| citric acid monohydrate | 0.06 |
| Nutrilan ® Keratin W PP[3] | 0.2 |
| Cosmedia ® Ultragel 300[4] | 2.0 |
| D-Panthenol 75% | 0.2 |
| Dehyquart ® F-75 T[5] | 1.8 |
| Crodazosoft ® DBQ[6] | 0.2 |
| Methylparaben | 0.1 |
| Phenoxyethanol | 0.4 |
| Silicon oil 50 cs | 3.0 |
| Dimethicone 5 cSt | 2.5 |
| fragrance | 0.8 |
| macadamia nut oil | 0.2 |
| water | to 100 |

*values in wt. %
[1] polyimide, Ashland
[2] polyvinylpyrrolidone/vinyl acetate copolymer; also Luviskol VA 64 W from BASF
[3] hydrolysed keratin (INCI)
[4] cationic polymer
[5] distearoylethyl hydroxyethylmonium methosulfate (INCI)
[6] quaternium-91 (INCI)

Two series of tests were performed with this composition as contemplated herein. In the first series of tests the composition as contemplated herein was tested in a "rinse-off" treatment. In the second series of tests the composition as contemplated herein was tested in a "leave-in" treatment.

In both series of tests the hair of test subjects was washed beforehand using a conventional shampoo.

In the first series of tests one half of the heads of the test subjects was treated, after washing, with the above composition as contemplated herein. The composition was massaged into the hair and left to act for one minute. The composition was then rinsed out, and the hair was dried. The results are shown in the table below, wherein the properties listed in the table were scored on a scale from 0 to 6, with 0 being the worst score.

| Property | Untreated | Treated |
| --- | --- | --- |
| Quality | 1.0 | 5.0 |
| Distribution on the hair | 1.0 | 5.5 |
| Easy formability | 1.0 | 5.0 |
| Movement (wet hair) | 4.0 | 5.0 |
| Feel (dry hair) | 5.0 | 5.0 |
| Feel (hair ends) | 5.0 | 5.0 |
| Bounce | 3.5 | 5.0 |
| Silkiness | 5.0 | 5.0 |
| Overburdening | 5.0 | 5.0 |
| Overall impression | 4.0 | 5.0 |

In the "rinse-off" treatment, as properties that can be observed macroscopically, the quality, formability and bounce in particular were improved after the treatment with the composition as contemplated herein.

In the second series of tests one half of the heads of the test subjects was treated, after washing, with the above composition as contemplated herein, whereas the other half of the head remained untreated. In this series of tests the "leave-in" treatment option was examined. The results are shown in the table below, wherein the properties listed in the table were scored on a scale from 0 to 6, with 0 being the worst score.

| Property | Untreated | Treated |
| --- | --- | --- |
| Quality | 1.0 | 5.0 |
| Distribution on the hair | 1.0 | 5.0 |
| Detangling of damp hair | 3.0 | 5.0 |
| Combability of damp hair | 4.0 | 5.0 |
| Feel of damp hair | 4.0 | 5.0 |
| Easy formability | 3.0 | 5.0 |
| Feel (dry hair) | 4.0 | 5.0 |
| Feel (hair ends) | 3.5 | 4.5 |
| Regulation of static charge | 4.0 | 5.0 |
| Shine | 4.0 | 5.0 |
| Bounce | 3.5 | 5.0 |
| Hair volume | 4.0 | 5.0 |
| Apparent degree of nourishment | 4.0 | 5.0 |
| Smoothness | 3.0 | 5.0 |
| Silkiness | 4.0 | 5.0 |
| Anti-frizz | 3.0 | 5.0 |
| Overburdening | 5.0 | 5.0 |
| Diffuser drier | 3.0 | 5.0 |

The results demonstrate the suitability of a composition as contemplated herein in a "leave-in" treatment.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent for treating keratin fibres, wherein the cosmetic agent in a cosmetic carrier comprises (a) at least one first polymer comprising the structural units of formulas M1, M2 and M3

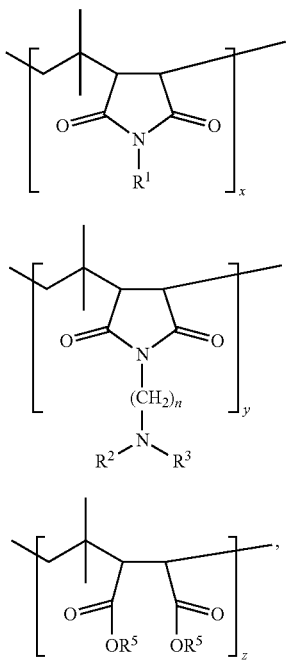

wherein
- R¹ is a group comprising oxyalkylene groups,
- R² and R³ independently of one another are an alkyl group comprising from about 1 to about 3 C atoms,
- n is a number between from about 1 and about 5, and
- R⁴ and R⁵ independently of one another are hydrogen or an alkyl group comprising from about 1 to about 3 C atoms, with the proviso that either R⁴ and R⁵ are hydrogen or one of R⁴ and R⁵ is hydrogen, wherein
- x, y and z each lie between about 0.05 and about 0.95 parts wherein the sum of x, y and z is equal to about 1, and (b) at least one second polymer, which is a film former, and (c) at least one first and one second siloxane, in each case comprising the structural units M5,

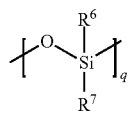

wherein the first siloxane is a low-molecular siloxane with q equal to 4 to 12, in which R⁶ and R⁷ are selected identically or differently from one another from H or an alkyl group comprising 1 to 4 C atoms, and wherein the second siloxane is a branched or unbranched polysiloxane with q greater than or equal to 20, in which R⁶ and R⁷ are selected identically or differently from one another from H or an alkyl group comprising 1 to 4 C atoms and wherein the first siloxane is included in the cosmetic agent in an amount of from about 0.5 to about 8 wt. %, in relation to the total weight of the cosmetic agent, and/or wherein the second siloxane is included in the cosmetic agent in an amount of from about 1 to about 10 wt. %, in relation to the total weight of the cosmetic agent, wherein the pH value of the cosmetic agent is between about 2 and about 5, and the viscosity is between about 8000 and about 25000 mPa s, measured at 20° C. with a Brookfield viscometer DV-II, spindle 6 at 20 rpm.

2. The cosmetic agent according to claim 1, wherein R¹ is chosen from a group comprising one or more oxyethylene groups and a group comprising one or more oxypropylene groups.

3. The cosmetic agent according to claim 1, wherein the first polymer is included in the cosmetic agent in an amount of from about 0.01 to about 2 wt. % in relation to the total weight of the cosmetic agent.

4. The cosmetic agent according to claim 1, wherein the second polymer representing the film former is derived from one or more monomer units comprising 1-vinyl-2-pyrrolidone.

5. The cosmetic agent according to claim 1, wherein the cosmetic agent comprises a third polymer which is a homopolymer comprising a poly(meth)acrylate with a quaternary ammonium alkylene group as ester side chain and a cosmetically acceptable counter ion.

6. The cosmetic agent according to claim 1, wherein the cosmetic agent comprises a cationic surfactant, wherein the cationic surfactant is chosen from one or more quaternary ammonium compounds.

7. A method for nourishing and shaping keratin fibres comprising the following steps:
applying a cosmetic agent to the keratin fibres in a first step wherein the cosmetic agent comprises
(a) at least one first polymer comprising the structural units of formulas M1, M2 and M3

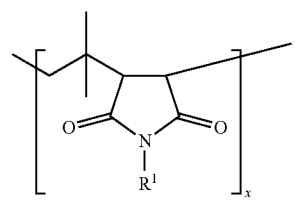

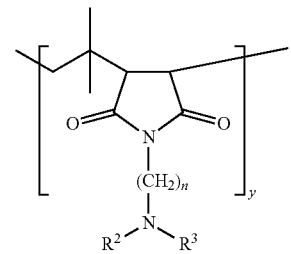

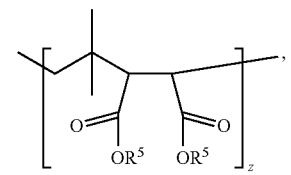

wherein
- R¹ is a group comprising oxyalkylene groups,
- R² and R³ independently of one another are an alkyl group comprising from about 1 to about 3 C atoms,
- n is a number between from about 1 and about 5, and
- R⁴ and R⁵ independently of one another are hydrogen or an alkyl group comprising from about 1 to about 3 C atoms, with the proviso that either $R^4$ and $R^5$ are hydrogen or one of $R^4$ and $R^5$ is hydrogen, wherein x, y and z each lie between about 0.05 and about 0.95 parts wherein the sum of x, y and z is equal to about 1, and (b) at least one second polymer, which is a film former, and (c) at least one first and one second siloxane, in each case comprising the structural units M5,

(M5)

wherein the first siloxane is a low-molecular siloxane with q equal to 4 to 12, in which $R^6$ and $R^7$ are selected identically or differently from one another from H or an alkyl group comprising 1 to 4 C atoms, and wherein the second siloxane is a branched or unbranched polysiloxane with q greater than or equal to 20, in which $R^6$ and $R^7$ are selected identically or differently from one another from H or an alkyl group comprising 1 to 4 C atoms and wherein the first siloxane is included in the cosmetic agent in an amount of from about 0.5 to about 8 wt. %, in relation to the total weight of the cosmetic agent, and/or wherein the second siloxane is included in the cosmetic agent in an amount of from about 1 to about 10 wt. %, in relation to the total weight of the cosmetic agent, wherein the pH value of the cosmetic agent is between about 2 and about 5, and the viscosity is between about 8000 and about 25000 mPa s, measured at 20° C. with a Brookfield viscometer DV-II, spindle 6 at 20 rpm, and leaving the cosmetic agent on the keratin fibres or rinsing the keratin fibres with water in a second step.

8. The cosmetic agent according to claim 1, wherein the pH value of the cosmetic agent is between from about 3 and about 4 and the viscosity is between 12000 and 16000, measured at 20° C. with a Brookfield viscometer DV-II, spindle 6 at 20 rpm.

9. The cosmetic agent according to claim 1, wherein $R^1$ is chosen from a group of general formula M4

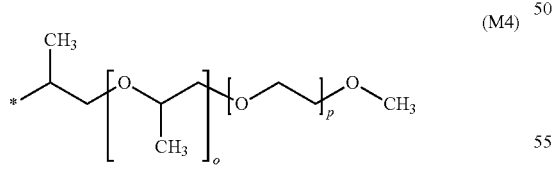

(M4)

in which o and p are each a number between about 1 and about 8, wherein $R^2$ and $R^3$ are each a methyl group and/or n is equal to about 3, or wherein $R^4$ and $R^5$ are either hydrogen or one of $R^4$ and $R^5$ is an ethyl group.

10. The cosmetic agent according to claim 1, wherein the first polymer is included in the cosmetic agent in an amount of from about from 0.2 to 0.5 wt. % in relation to the total weight of the cosmetic agent.

11. The cosmetic agent according to claim 1, wherein the second polymer representing the film former is derived from the monomer units 1-vinyl-2-pyrrolidone and vinyl acetate in a ratio of 1-vinyl-2-pyrrolidone to vinyl acetate of greater than 1.

12. The cosmetic agent according to claim 11, wherein the second polymer representing the film former is included in the cosmetic agent in an amount of from about 4 to about 6 wt. %, in relation to the total weight of the cosmetic agent.

13. The cosmetic agent according to claim 5, wherein the third polymer is a homopolymer derived from the monomer N, N, N-trimethyl-2-((2-methyl-1-oxo-2-propenyl)oxy) chloride.

14. The cosmetic agent according to claim 13, wherein the third polymer is included in the cosmetic agent in an amount of from about 0.1 to about 5 wt. % in relation to the total weight of the cosmetic agent.

15. The cosmetic agent according to claim 1, wherein the first siloxane is the low-molecular siloxane with q equal to from about 6 to about 10, in which $R^6$ and $R^7$ are the same and are a methyl group, and wherein the second siloxane is a branched or unbranched polysiloxane with q greater than or equal to 20, in which $R^6$ and $R^7$ are the same and are a methyl group.

16. The cosmetic agent according to claim 1, wherein the first siloxane is included in the cosmetic agent in an amount of from about 2 to about 3 wt. %, in relation to the total weight of the cosmetic agent, and wherein the second siloxane is included in the cosmetic agent in an amount of from about 4 to about 6 wt. %, in relation to the total weight of the cosmetic agent.

17. A cosmetic agent for treating keratin fibres, wherein the cosmetic agent in a cosmetic carrier comprises (a) at least one first polymer comprising the structural units of formulas M1, M2 and M3

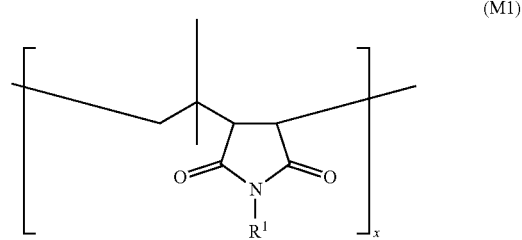

(M1)

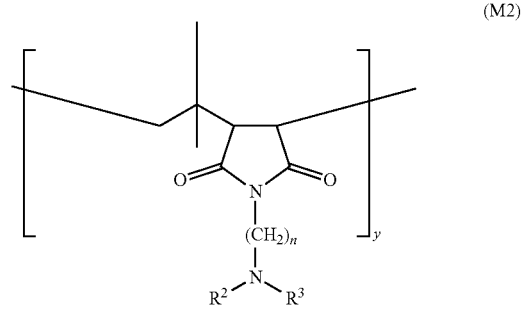

(M2)

(M3)

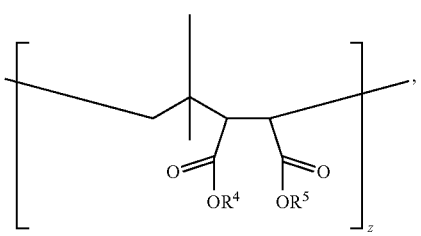

wherein
R¹ is chosen from a group of general formula M4

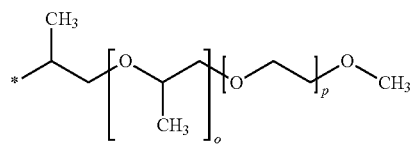
(M4)

in which o and p are each a number between about 1 and about 50,

R² and R³ independently of one another are an alkyl group comprising from about 1 to about 3 C atoms, n is a number between from about 1 and about 5, and R⁴ and R⁵ independently of one another are hydrogen or an alkyl group comprising from about 1 to about 3 C atoms, with the proviso that either R⁴ and R⁵ are hydrogen or one of R⁴ and R⁵ is hydrogen, wherein x, y and z each lie between about 0.05 and about 0.95 parts wherein the sum of x, y and z is equal to about 1, wherein the first polymer is included in the cosmetic agent in an amount of from about 0.01 to about 2 wt. %, and (b) at least one second polymer, which is a film former, wherein the second polymer representing the film former is derived from the monomer units 1-vinyl-2-pyrrolidone and vinyl acetate, wherein the second polymer representing the film former is included in the cosmetic agent in an amount of from about 1 to about 9 wt. % in relation to the total weight of the cosmetic agent, and (c) at least one first and one second siloxane, in each case comprising the structural units M5,

(M5)

wherein the first siloxane is a low-molecular siloxane with q equal to 4 to 12, in which R⁶ and R⁷ are selected identically or differently from one another from H or an alkyl group comprising 1 to 4 C atoms, and wherein the second siloxane is a branched or unbranched polysiloxane with q greater than or equal to 20, in which R⁶ and R⁷ are selected identically or differently from one another from H or an alkyl group comprising 1 to 4 C atoms and wherein the first siloxane is included in the cosmetic agent in an amount of from about 0.5 to about 8 wt. %, in relation to the total weight of the cosmetic agent, and/or wherein the second siloxane is included in the cosmetic agent in an amount of from about 1 to about 10 wt. %, in relation to the total weight of the cosmetic agent, wherein the pH value of the cosmetic agent is between from about 3 and about 4 and the viscosity is between 12000 and 16000, measured at 20° C. with a Brookfield viscometer DV-II, spindle 6 at 20 rpm.

18. The cosmetic agent according to claim 17, wherein the cosmetic agent comprises a third polymer which is a homopolymer comprising a poly(meth)acrylate with a quaternary ammonium alkylene group as ester side chain and a halide counter ion, wherein the third polymer is included in the cosmetic agent in an amount of from about 0.1 to about 5 wt. % in relation to the total weight of the cosmetic agent.

* * * * *